(12) United States Patent
Dahlgren et al.

(10) Patent No.: US 11,951,276 B2
(45) Date of Patent: Apr. 9, 2024

(54) FLUID INJECTION SYSTEM WITH ILLUMINATED FLUID RESERVOIR

(71) Applicant: ACIST Medical Systems, Inc., Eden Prairie, MN (US)

(72) Inventors: Aron David Dahlgren, Edina, MN (US); Blaise D. Porter, Minneapolis, MN (US)

( * ) Notice: Subject to any disclaimer, the term of this patent is extended or adjusted under 35 U.S.C. 154(b) by 721 days.

(21) Appl. No.: 16/931,997

(22) Filed: Jul. 17, 2020

(65) Prior Publication Data

US 2022/0016333 A1  Jan. 20, 2022

(51) Int. Cl.
*A61M 5/00* (2006.01)
*A61M 5/36* (2006.01)

(52) U.S. Cl.
CPC ............ *A61M 5/007* (2013.01); *A61M 5/365* (2013.01); *A61M 2205/3334* (2013.01); *A61M 2205/583* (2013.01); *A61M 2205/587* (2013.01)

(58) Field of Classification Search
CPC .................. A61M 5/007; A61M 5/365; A61M 2205/3334; A61M 2205/587; A61M 2205/583; A61M 2005/3114; A61M 5/16886; A61M 5/1684; A61M 5/31568; A61M 2205/3389; A61M 2205/3306; A61M 2205/50
See application file for complete search history.

(56) References Cited

U.S. PATENT DOCUMENTS

| | | | |
|---|---|---|---|
| 2009/0177155 A1* | 7/2009 | Schriver | A61M 5/14546 604/131 |
| 2015/0088092 A1* | 3/2015 | Holm | A61M 5/5086 604/506 |
| 2016/0296716 A1* | 10/2016 | Cabiri | A61M 5/5086 |
| 2017/0056604 A1* | 3/2017 | Cowan | G01F 23/02 |
| 2019/0054252 A1* | 2/2019 | Amschler | A61M 5/24 |
| 2022/0211954 A1† | 7/2022 | Cowan | |

FOREIGN PATENT DOCUMENTS

WO   WO-2019145318 A1 *  8/2019  .......... A61M 5/1452

OTHER PUBLICATIONS

ACIST CVi® Contrast Delivery System brochure (2016), pp. 1-8.
PCT International Search Report and Written Opinion dated Oct. 26, 2021 for related International Application No. PCT/US2021/041914, 9 pages.

\* cited by examiner
† cited by third party

*Primary Examiner* — Nilay J Shah
(74) *Attorney, Agent, or Firm* — Carlson, Caspers, Vandenburgh & Lindquist, P.A.

(57) ABSTRACT

A fluid injection system includes an injector housing, a sleeve, and a lighting assembly. The sleeve is coupled to the injector housing and is configured to receive and secure a fluid reservoir. The lighting assembly is coupled to the injector housing. The lighting assembly includes a light source configured to illuminate an interior of the fluid reservoir by directing light emitted by the light source into the fluid reservoir.

8 Claims, 11 Drawing Sheets

FLUID INJECTION SYSTEM WITH ILLUMINATED FLUID RESERVOIR

TECHNICAL FIELD

The disclosure relates to fluid injection systems.

BACKGROUND

Many medical imaging procedures, such as angiography, involve injecting a contrast fluid into a patient. Angiography is a procedure used in the diagnosis and treatment of cardiovascular conditions, including abnormalities or restrictions in blood vessels. During angiography, a radiographic image of the heart or vascular structure is obtained by injecting contrast fluid through a catheter into the vasculature (e.g., the coronary artery) of the patient. The injected contrast fluid can pass to vascular structures in fluid communication with the blood vessel in which the injection is made. X-rays are passed through the region of the body in which the contrast fluid was injected. The X-rays are absorbed by the contrast fluid, causing a radiographic outline or image of the vasculature containing the contrast fluid. Contrast injection can be used in conjunction with other medical procedures as well, such as optical coherence tomography (OCT) imaging, intravascular ultrasound (IVUS) imaging, computed tomography (CT) imaging, magnetic resonance imaging (MRI), and interventional device procedures/placements.

SUMMARY

In general, the disclosure describes a fluid injection system with a light source particularly configured to illuminate the interior of a fluid reservoir. In some instances, the light source illuminates the interior of the fluid reservoir by shining through one end of the fluid reservoir and using the liquid inside the fluid reservoir to refract the light such that it illuminates the interior of the fluid reservoir. In other instances, the light source focuses and directs light towards a reflector that reflects the light down a peripheral wall of the fluid reservoir.

In any instance, providing a light particularly configured to illuminate the interior of the fluid reservoir provides numerous benefits. For example, if there are bubbles in the fluid reservoir, it could be harmful to the patient in which the fluid is to be injected, as injecting air into a patient's body could have adverse effects on their health. In these instances, a light configured to illuminate the interior of the fluid reservoir may ease the identification of such bubbles within the fluid reservoir, as opposed to relying on any ambient light that happens to enter the fluid reservoir from an outside source.

In other instances, the light may provide additional functionality above and beyond merely illuminating the interior of the fluid reservoir for bubble identification. For instance, the light source may be configured to change a characteristic about the light itself based on operating status of the fluid injection system. The light source may utilize various light characteristics, such as a brightness, a color, a flashing pattern, a number of individual lights within the light source to be illuminated, or some combination thereof, to provide information regarding one or more of an injection rate, a volume of fluid contained in the fluid reservoir, an air bubble detection mode, an injection mode, a refill rate, or an error status. When a user is operating the fluid injection system, the user must monitor a number of objects, including the patient, the injection site, the injection fluid, the controller, any displays being generated, and other staff assisting with the patient. By utilizing light characteristics to signal the operating status of the fluid injection system, the fluid injection system reduces the number of devices that the user must monitor in order to derive important information, and may also reduce the amount of data that must be produced and output by the controller.

In one example, the disclosure is directed to a fluid injection system. The fluid injection system includes an injector housing. The fluid injection system also includes a sleeve coupled to the injector housing. The sleeve is configured to receive and secure a fluid reservoir. The fluid injection system further includes a lighting assembly coupled to the injector housing. The lighting assembly includes a light source configured to illuminate an interior of the fluid reservoir by directing light emitted by the light source into the fluid reservoir.

In another example, the disclosure is directed to a method that includes controlling, by one or more processors of a fluid injection system, a light source in a lighting assembly of the fluid injection system to illuminate an interior of a fluid reservoir by directing light emitted by the light source into the fluid reservoir, wherein the fluid reservoir is secured by a sleeve coupled to an injector housing of the fluid injection system. The method further includes determining, by the one or more processors of the fluid injection system, an operating status of the fluid injection system. The method also includes setting, by the one or more processors, one or more characteristics of the light source to be indicative of the operating status of the fluid injection system.

In another example, the disclosure is directed to a non-transitory computer-readable storage medium containing instructions. The instructions, when executed, cause one or more processors to control a light source in a lighting assembly of the fluid injection system to illuminate an interior of a fluid reservoir secured by a sleeve coupled to an injector housing of the fluid injection system. The instructions, when executed, further cause one or more processors to determine an operating status of the fluid injection system. The instructions, when executed, also cause one or more processors to set one or more characteristics of the light source to be indicative of the operating status of the fluid injection system.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
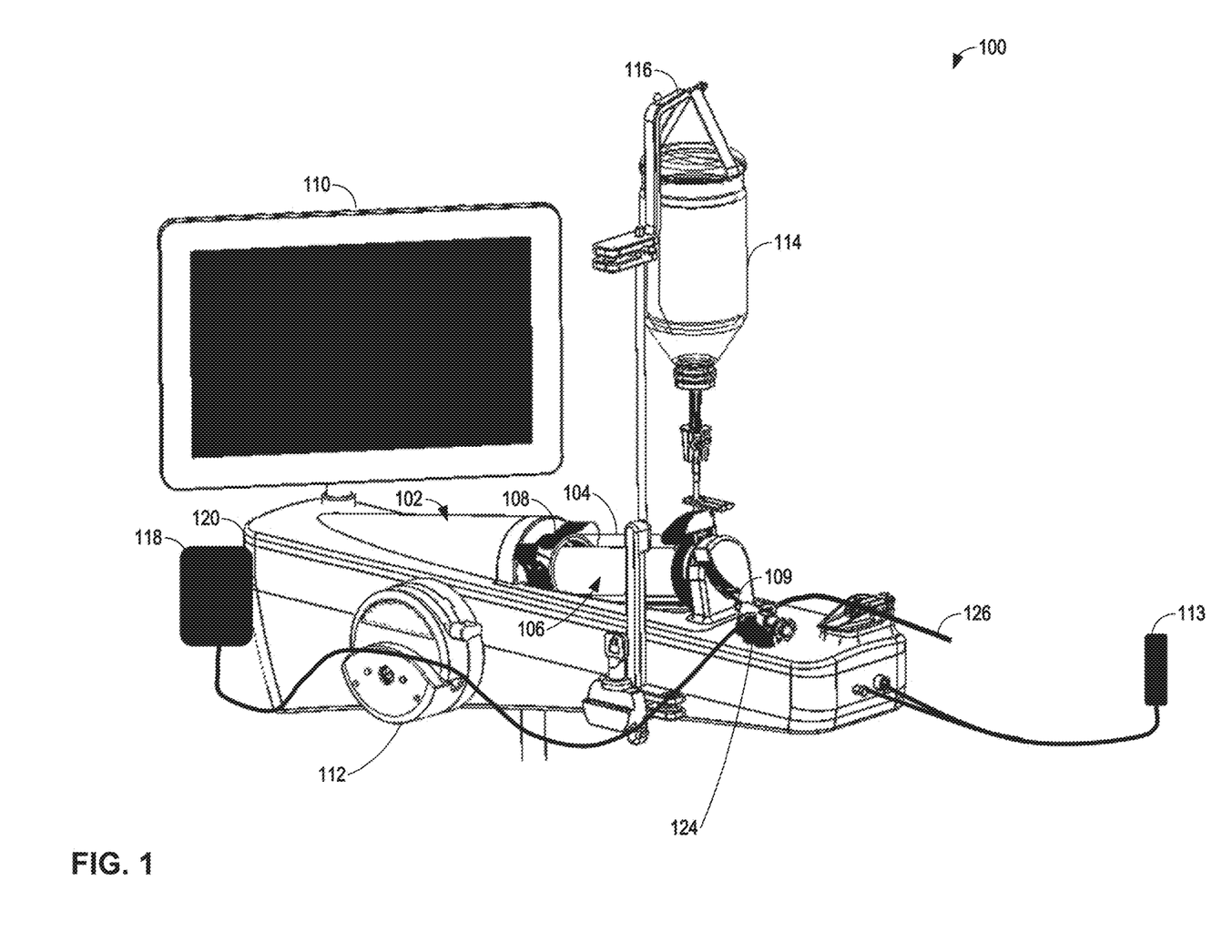
FIG. 1 is a perspective view of an example of a powered fluid injector, in accordance with one or more aspects of the techniques described in this disclosure.

FIG. 1 is a perspective view of an example of a powered fluid injector 100. In operation, the powered fluid injector 100 can inject a quantity of fluid into a patient, for instance into a vessel of a patient via a catheter. The fluid injected by the powered fluid injector 100 can be, for example, a contrast fluid, a non-contrast fluid (e.g., saline), or a combination thereof. By injecting a quantity of fluid into a patient, the powered fluid injector 100 can facilitate a variety of medical diagnostic and/or interventional procedures, including the collection of image data representing an anatomical region of interest. These procedures can include, as examples, optical coherence tomography (OCT) imaging, intravascular ultrasound (IVUS) imaging, computed tomography (CT) imaging, magnetic resonance imaging (MRI), angiographic procedures, and interventional device procedures/placements.

The illustrated powered fluid injector 100 includes a drive assembly housing 102 (also referred to herein as an "injector housing") and a sleeve 104. The sleeve 104 can be secured to the drive assembly housing 102. For example, the drive assembly housing 102 can include an opening, and the sleeve 104 can be secured to the drive assembly housing 102 at or near such opening. The sleeve 104 may extend out from the drive assembly housing 102 and may be configured to receive and hold a fluid reservoir 106 (also referred to herein as a "fluid reservoir"). The fluid reservoir 106 can have an internal reservoir volume containing a fluid and can include a plunger 108 within the internal reservoir volume. Plunger 108 may be made of various components, including a wiper configured to be proximally and distally movable within the interior of fluid reservoir 106 and a ram extending from drive assembly housing 102 into sleeve 104 and being configured to engage the wiper when fluid reservoir 106 is received and secured in sleeve 104 and to drive the wiper proximally and distally in accordance with instructions received from controller 110 coupled to drive assembly housing 102. At least a portion of a drive assembly can be housed within the drive assembly housing 102.

The drive assembly can be configured to pressurize fluid within the internal reservoir volume. For instance, the drive assembly may couple to the plunger 108, such as at the opening in the drive assembly housing 102, and drive the plunger 108 within the internal reservoir volume. As the plunger 108 is progressively driven within the fluid reservoir 106, fluid within the internal reservoir volume can be output from the fluid reservoir 106 along tubing 109 leading to a catheter 126 that is inserted into a patient's blood vessel to inject the fluid into the vasculature. In certain applications of the powered fluid injector 100, output fluid, such as contrast media, can be pressurized anywhere from 1000-1500 psi (e.g., 1200 psi).

The illustrated example of the powered fluid injector 100 includes several features that can be useful in pressurizing and delivering fluid during operation. The powered fluid injector 100 can include a controller 110. The controller 110 can include a user interface for various operational aspects. For example, the controller 110 can be utilized by a user to set up various parameters and/or protocols to be used for a given fluid injection procedure. In one example, the user can interact with the controller 110 to input fluid injection parameters such as flow rate, injection volume (e.g., maximum), injection pressure limit (e.g., maximum), fluid injection duration, rise time, and/or other injection parameters. In one example, the controller 110 includes a touch-screen panel display, enabling a user to view and modify injection parameters. The controller 110 can also be used to initialize the powered fluid injector 100 (e.g., to prepare it for a patient fluid injection), or to activate certain features or sequences of operation. The controller 110 may also provide status information, including information related to past or currently ongoing injection procedures as well as any appropriate alerts. The controller 110 can include an imaging engine having one or more processors for controlling operation of the powered fluid injector 100. Such processors can also control other components, such as the drive assembly, a peristaltic pump 112, when present, and/or any sensors and detectors included at the powered fluid injector 100.

In addition to the controller 110, the illustrated powered fluid injector 100 includes a hand-control device 113 for user input. The hand-control device 113 can be coupled to the controller 110 either wirelessly or via a lined connection. Although in other examples, the hand-control device 113 can be connected to a component of the powered fluid injector 100 other than the controller 110, such as drive assembly housing 102. The hand-control device 113 can generate and send various signals related to an injection procedure to the controller 110 or other connected component. A user can actuate one or more interface components at the hand-control device 113 to control an injection procedure. For example, the user can use hand-control device 113 as a variable-rate control device to alter the fluid flow rate output from the powered fluid injector 100 and/or as a mechanism for starting or stopping a fluid injection. Hand-control device 113 may include an exterior body of the controller that is sized to be held in a single hand of a user. In other instances, hand-control device 113 may be sized differently, such as to be held in two hands of the user or to sit on a surface during operation.

The powered fluid injector 100 can also include one or more components useful for supplying fluid to be used in an injection procedure. A container 114 can include a supply of fluid, such as contrast media, and be secured to a holder 116 at the powered fluid injector 100. Fluid from the container 114 can be supplied to the fluid reservoir 106 for use during an injection procedure. For example, fluid from the container 114 can be drawn into the fluid reservoir 106 when the plunger 108 is being retracted (e.g., moved in a direction toward the drive assembly housing 102) and thereby refill the internal reservoir volume. Similarly, when the powered fluid injector 100 includes the peristaltic pump 112, a second container 118 can include a supply of fluid, such as a flushing medium (e.g., saline), and be secured to a holder 120 at the powered fluid injector 100. When present, the peristaltic pump 112 can receive fluid from the second container 118 and deliver such fluid to the patient. Often times, the peristaltic pump 112 may be used to deliver non-contrast fluid, such as saline, at a lower pressure than that at which the drive assembly delivers contrast fluid from the fluid reservoir 106. A valving system 124 can be included to selectively place the fluid reservoir 106 or peristaltic pump 112 in communication with the patient.

As described elsewhere herein, the controller 110 of the powered fluid injector 100 may control various functions of the powered fluid injector 100, which may include dispensing contrast fluid out through tubing. In some examples, the controller 110 may be housed in a housing of a display device. In some examples, the controller may be housed in the injector housing.

The powered fluid injector may be connected to a catheter 126, fluidly and electrically, that is inserted into a blood vessel (e.g., the coronary artery) of a patient. When so connected, the powered fluid injector can inject contrast fluid or dispense non-contrast fluid into the patient's vasculature via the injector tubing and the catheter 126. In many examples, the catheter 126 may include an invasive blood pressure sensor. The blood pressure sensor may be in electrical communication with the controller when the powered fluid injector is connected to the catheter 126. The blood pressure sensor may provide a blood pressure signal to the controller when the catheter 126 is in fluidic connection with the powered fluid injector and may not provide a blood pressure signal when the catheter 126 is not in fluidic connection with the powered fluid injector.

In accordance with one or more techniques of this disclosure, powered fluid injector 100 may also include a lighting assembly coupled to drive assembly housing 102. The lighting assembly may include a light source configured to illuminate an interior of fluid reservoir 106 by directing light emitted by the light source into fluid reservoir 106, such as substantially parallel to a long axis of fluid reservoir 106.

In some instances, the light source illuminates the interior of fluid reservoir 106 by directing light through one end of fluid reservoir 106 and using the fluid volume inside fluid reservoir 106 to reflect and refract the light such that it spreads the light throughout the fluid to illuminate the interior of fluid reservoir 106. In other instances, the light source illuminates the interior of fluid reservoir 106 by focusing and directing light towards a reflector that reflects the light down a peripheral wall of fluid reservoir 106. In still other instances, a diffuser is installed in fluid injector 100, such as in drive assembly housing 102, pressure sleeve 104, or in fluid reservoir 106, such that the diffuser separates the light source from the interior of fluid reservoir 106 and such that the diffuser diffuses the light emitted by the light source as it enters the interior of fluid reservoir 106.

In any instance, providing a light particularly configured to illuminate the interior of fluid reservoir 106 provides numerous benefits. For example, if there are air bubbles in within the fluid volume of fluid reservoir 106, it could be harmful to the patient in which the fluid is to be injected, as injecting air into a patient's body could have adverse effects on their health. In these instances, a light configured to illuminate the interior of fluid reservoir 106 may ease the identification of such air bubbles within fluid reservoir 106, as opposed to relying on any ambient light that happens to enter fluid reservoir 106 from an outside source.

In other instances, the light may provide additional functionality other than merely illuminating the interior of fluid reservoir 106 for bubble identification. For instance, the light source may be configured to change a characteristic about the light itself based on operating status of powered fluid injector 100. The light source may utilize various light characteristics, such as a brightness, a color, a flashing pattern, a number of individual lights within the light source to be illuminated, or some combination thereof, to provide information regarding one or more of an injection rate, a volume of fluid contained in the fluid reservoir, an air bubble detection mode, an injection mode, a refill rate, or an error status. When a user is operating powered fluid injector 100, the user must monitor a number of objects, including the patient, the injection site, the fluid volume, controller 110, any displays being generated, and other staff assisting with the patient. By utilizing light characteristics to signal the operating status of powered fluid injector 100, powered fluid injector 100 reduces the number of devices that the user must monitor in order to derive important information, and may also reduce the amount of data that must be produced and output by controller 110.

Figure 2:
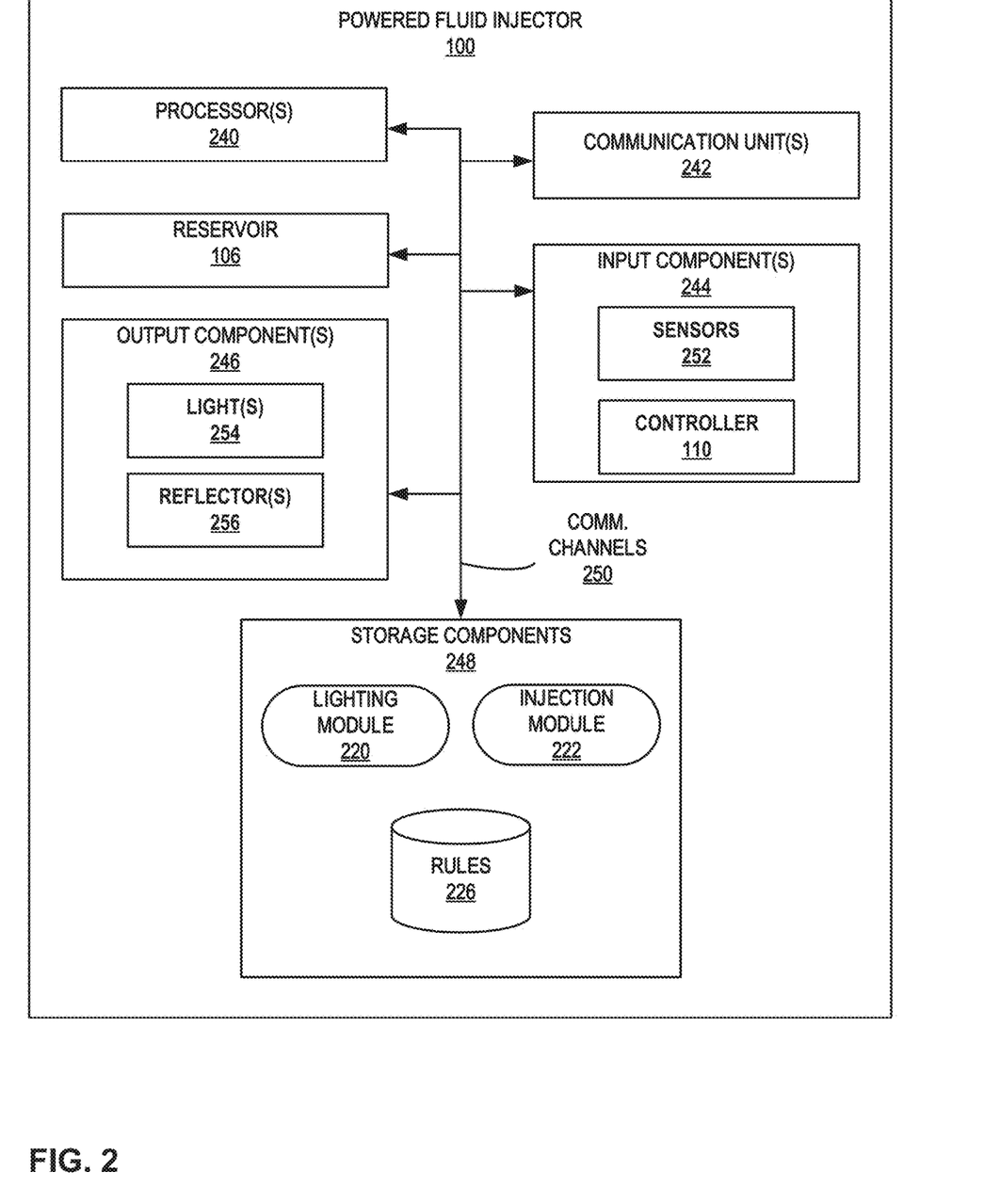
FIG. 2 is a block diagram illustrating a more detailed example of a computing device configured to perform the techniques described herein.

FIG. 2 is a block diagram illustrating an example fluid injection system configured to utilize a light source to illuminate a fluid reservoir, in accordance with one or more aspects of the techniques described in this disclosure. Powered fluid injector 100 of FIG. 2 is described below as an example of powered fluid injector 100 of FIG. 1. FIG. 2 illustrates only one particular example of powered fluid injector 100, and many other examples of powered fluid injector 100 may be used in other instances and may include a subset of the components included in example powered fluid injector 100 or may include additional components not shown in FIG. 2.

As shown in the example of FIG. 2, powered fluid injector 100 includes fluid reservoir 106, one or more processors 240, one or more communication units 242, one or more input components 244, one or more output components 246, and one or more storage components 248. Input components 244 may include sensors 252 and controller 110. Output components 246 may include light source 254 (also referred to herein as "lights 254") and one or more reflectors 256. Storage components 248 of powered fluid injector 100 include lighting module 220, injector module 222, and rules data store 226.

One or more processors 240 may implement functionality and/or execute instructions associated with powered fluid injector 100 to operate lights 254 to illuminate an interior of fluid reservoir 106 of powered fluid injector 100. That is, processors 240 may implement functionality and/or execute instructions associated with powered fluid injector 100 to control one or more characteristics of lights 254 to illuminate the interior of fluid reservoir 106, either for the function of revealing bubbles within a fluid volume held by fluid reservoir 106 or to convey an operating status of powered fluid injector 100 (or for both purposes).

Examples of processors 240 include application processors, display controllers, auxiliary processors, one or more sensor hubs, and any other hardware configure to function as a processor, a processing unit, or a processing device. Modules 220 and 222 may be operable by processors 240 to perform various actions, operations, or functions of powered fluid injector 100. For example, processors 240 of powered fluid injector 100 may retrieve and execute instructions stored by storage components 248 that cause processors 240 to perform the operations described with respect to modules 220 and 222. The instructions, when executed by processors 240, may cause powered fluid injector 100 to operate lights 254 to illuminate an interior of fluid reservoir 106 of powered fluid injector 100.

Lighting module 220 may include all functionality for operating lights 254 of powered fluid injector 100. For example, lighting module 220 of powered fluid injector 100 may receive information from injection module 222 and control one or more characteristics of lights 254, such as whether to turn lights 254 on, what color to use for lights 254, or what pattern to use for flashing lights 254.

Injection module 222 may include all functionality for controlling other aspects of powered fluid injector 100. In some examples, injection module 222 may communicate, via communication units 242, with sensors 252 and controller 110 to determine an operating status of powered fluid injector 100. In some examples, injection module 222 may determine one or more of one or more of an injection rate, a volume of fluid contained in the fluid reservoir, an air bubble detection mode, an injection mode, a refill rate, or an error status for powered fluid injector 100.

One or more storage components 248 within powered fluid injector 100 may store information for processing during operation of powered fluid injector 100 (e.g., powered fluid injector 100 may store data accessed by modules 220 and 222 during execution at powered fluid injector 100). In some examples, storage component 248 is a temporary memory, meaning that a primary purpose of storage component 248 is not long-term storage. Storage components 248 on powered fluid injector 100 may be configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage components 248, in some examples, also include one or more computer-readable storage media. Storage components 248 in some examples include one or more non-transitory computer-readable storage mediums. Storage components 248 may be configured to store larger amounts of information than typically stored by volatile memory. Storage components 248 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage components 248 may store program instructions and/or information (e.g., data) associated with modules 220 and 222 and data store 226. Storage components 248 may include a memory configured to store data or other information associated with modules 220 and 222 and data store 226.

Communication channels 250 may interconnect each of the components 106, 240, 242, 244, 246, and 248 for inter-component communications (physically, communicatively, and/or operatively). In some examples, communication channels 250 may include a system bus, a network connection, an inter-process communication data structure, or any other method for communicating data.

One or more communication units 242 of powered fluid injector 100 may communicate with external devices via one or more wired and/or wireless networks by transmitting and/or receiving network signals on one or more networks. Examples of communication units 242 include a network interface card (e.g., such as an Ethernet card), an optical transceiver, a radio frequency transceiver, a GPS receiver, or any other type of device that can send and/or receive information via a wireless or wired connection. Other examples of communication units 242 may include short wave radios, cellular data radios, wireless network radios, as well as universal serial bus (USB) controllers.

One or more input components 244 of powered fluid injector 100 may receive input. Examples of input are tactile, audio, and video input. Input components 244 of powered fluid injector 100, in one example, includes a presence-sensitive input device (e.g., a touch sensitive screen, a PSD), mouse, keyboard, voice responsive system, camera, microphone or any other type of device for detecting input from a human or machine. For instance, controller 110 may be one of input components 244. In some examples, input components 244 may include one or more sensor components 252 one or more location sensors (GPS components, Wi-Fi components, cellular components), one or more temperature sensors, one or more movement sensors (e.g., accelerometers, gyros), one or more pressure sensors (e.g., barometer), one or more ambient light sensors, and one or more other sensors (e.g., infrared proximity sensor, hygrometer sensor, and the like). Other sensors, to name a few other non-limiting examples, may include a heart rate sensor, magnetometer, glucose sensor, olfactory sensor, compass sensor, or a step counter sensor.

One or more output components 246 of powered fluid injector 100 may generate output in a selected modality. Examples of modalities may include a tactile notification, audible notification, visual notification, machine generated voice notification, or other modalities. Output components 246 of powered fluid injector 100, in one example, includes a presence-sensitive display, sound card, video graphics adapter card, speaker, cathode ray tube (CRT) monitor, liquid crystal display (LCD), or any other type of device for generating output to a human or machine in a selected modality. Output components 246 may include lights 254, which may be one or more of a variety of types of lights, such as light emitting diodes, fluorescent lights, or any other type of light source that could illuminate fluid reservoir 106. Output components 246 may also include one or more reflectors 256, which may be used to direct and/or focus light emitting from lights 254 to more effectively illuminate at least a portion of the interior of fluid reservoir 106.

In accordance with the techniques described herein, a sleeve (e.g., sleeve 104) may be configured to receive and secure fluid reservoir 106. Lights 254 may be included within a lighting assembly coupled to an injector housing of powered fluid injector 100. Lights 254 may be configured to illuminate an interior of fluid reservoir 106 by directing light emitted by the light source into fluid reservoir 106, such as by directing the light, either upon emission from lights 254 or after a reflection of the light after emission from lights 254, at least substantially parallel to a long axis of fluid reservoir 106. For the purposes of this disclosure, a long axis of fluid reservoir 106 comprises an axis that, when drawn from one end of fluid reservoir 106 to the other, is an axis that is the longest possible straight line that is also perpendicular with the end caps of each end of fluid reservoir 106 when fluid reservoir 106 is a cylinder. Being substantially parallel to the long axis may mean that the light, when it is emitted from lights 254, is on a projected path that is within a small deviation of being parallel to the long axis, such as within fifteen degrees of a line that would be parallel to the long axis of fluid reservoir 106.

Lighting module 220 may be configured to operate lights 254 such that lights 254 may illuminate the interior of fluid reservoir 106. Processors 240 may control lighting module 220 to control one or more characteristics of lights 254 when illuminating the interior of fluid reservoir 106. The one or more characteristics of lights 254 may include one or more of a brightness, a color, a flashing pattern, or a number of individual lights within the light source to be illuminated.

Injection module 222 may further determine an operating status of powered fluid injector 100. The operating status of powered fluid injector 100 could include one or more of an injection rate, a volume of fluid contained in the fluid reservoir, an air bubble detection mode, an injection mode, a refill rate, or an error status. Lighting module 220 may set the one or more characteristics of the light source to be indicative of the operating status of the fluid injection system according to rules data store 226. Lighting module 220 may also control the one or more characteristics of lights 254 based on instructions received from controller 110 coupled to the injector housing.

For instance, injection module 222 may determine that an error has occurred in powered fluid injector 100. As such, lighting module 220 may determine that, according to rules data store 226, lights 254 should be illuminated in a red color with a slow flashing pattern. As such, lighting module 220 may control lights 254 to illuminate such that they are red in color and flash according to the error pattern.

In other instances, injection module 222 may determine that the volume of fluid within fluid reservoir 106 is a maximum amount of fluid that may be held by fluid reservoir 106. Rules 226 may include a rule that the color moves along a gradient from green to red as the volume of fluid within reservoir decreases. As such, lighting module 220 may control lights 254 to illuminate with a green color.

In still other instances, rules 226 may include a rule that a number of lights in lights 254 increases as the injection rate increases, thereby increasing the brightness of the light within fluid reservoir 106. Injection module 222 may determine that powered fluid injector 100 is injecting fluid into a patient a rate equal to 50% of the maximum injection rate. As such, lighting module 220 may control lights 254 such that only half of lights 254 are illuminated.

In other instances, rules 226 may include a rule that, when in air bubble detection mode, lights 254 should be illuminated with a white light at a maximum brightness. Injection module 222 may determine that powered fluid injector 100 is in such an air bubble detection mode. As such, lighting module 220 may control lights 254 such that lights 254 are illuminated in a white color at a maximum brightness.

In some instances, fluid reservoir 106 includes a peripheral wall that defines the interior of fluid reservoir 106. The peripheral wall may extend between a proximal edge of fluid reservoir 106 and a distal edge of fluid reservoir 106. In some such instances, lights 254 may be configured to illuminate the interior of fluid reservoir 106 by directing light along the peripheral wall of fluid reservoir 106. Lights 254 may direct the light along the peripheral wall of fluid reservoir 106 by directing light into the proximal edge of the fluid reservoir, along the peripheral wall of fluid reservoir 106, and toward the distal edge of fluid reservoir 106—in many cases by directing light into reflector 256 which reflects the light into the proximal edge of fluid reservoir 106, along the peripheral wall of fluid reservoir 106, and toward the distal edge of fluid reservoir 106. Lights 254 may also direct the light along the peripheral wall of fluid reservoir 106 by directing light into the distal edge of fluid reservoir 106, along the peripheral wall of the fluid reservoir, and toward the proximal edge of fluid reservoir 106. In the instances where the light is directed along a peripheral wall of fluid reservoir 106, the peripheral wall may include imperfections, such as chips, additional patterns interfering with the light, or other diffusion mechanisms such that the light may escape the peripheral wall to provide adequate lighting of fluid reservoir 106.

In some instances, fluid reservoir 106 may also include a plunger, such as plunger 108 of FIG. 1. The plunger may include a wiper that is proximally and distally movable within the interior of fluid reservoir 106. The plunger may also include a ram extending from the injector housing into the sleeve, the ram being configured to engage the wiper when fluid reservoir 106 is received and secured in the sleeve and to drive the wiper proximally and distally in accordance with instructions received from controller 110 coupled to the injector housing.

In some instances, fluid injection system 100 may also include a diffusion element, which may be located between lights 254 and fluid reservoir 106. In this way, the light emitted by lights 254 passes through the diffusion element on its path into fluid reservoir 106. For instance, lights 254 may be located either outside of an endcap of fluid reservoir 106 or in a plunger in fluid reservoir 106. The diffusion element may be located between lights 254 and the location where the light would enter fluid reservoir 106, such as within a housing of fluid injector 100, in the endcap of fluid reservoir 106, in a pressure sleeve that holds fluid reservoir 106, or in the plunger of fluid reservoir 106. The diffusion element may be configured to diffuse the light emitted by lights 254 as it enters fluid reservoir 106 in order to illuminate the entirety of fluid reservoir 106. In order to accomplish this, the diffusion element may be made of a clear material, or at least include a pattern of a substantially translucent material that diffuses the light as it passes through the diffusion element. For instance, the diffusion element may be at least partially made of a material such as a clear plastic, silicone, glass, frosted glass, or any other material that substantially allows light to pass through it. The pattern in the diffusion element, such as a waffle pattern or bubble pattern, may further enable the diffusion of the light as it passes through the diffusion element.

Lights 254, in some examples, may also be very bright, depending on the type of bulb included in lights 254. While this can be beneficial in many instances, the brightness of lights 254 may be distracting or even harmful to the user if lights 254 are uncovered and/or unfiltered. The diffusion element, when included in fluid injector 100, may reduce the intensity of the glare produced by lights 254, thereby creating a healthier and more pleasant user experience.

FIGS. 3A-3E are views of various examples of a fluid reservoir 106 and lights 254 configured to illuminate an interior of the fluid reservoir, in accordance with one or more aspects of the techniques described in this disclosure. In each of examples 3A-3E, fluid reservoir 106 includes plunger 108 and peripheral wall 330. In the examples of FIG. 3A-3E, peripheral wall 330 is a top-most portion of the exterior wall in fluid reservoir 106 when fluid reservoir 106 is substantially horizontal. In other examples, peripheral wall 330 may be any other wall of fluid reservoir 106, such as a bottom-most portion of the exterior wall or a lateral-most portion of the exterior wall when fluid reservoir 106 is substantially horizontal. In still other examples, peripheral wall 330 includes the entirety of the exterior wall of fluid reservoir 106, and lighting peripheral wall 330 includes lighting the entire circumference of the exterior wall of fluid reservoir 106. In any of FIGS. 3A-3E, lights 254 may be operable by a fluid injection system to illuminate fluid reservoir 106, in accordance with the description of lights 254 throughout this disclosure.

Figure 3A:
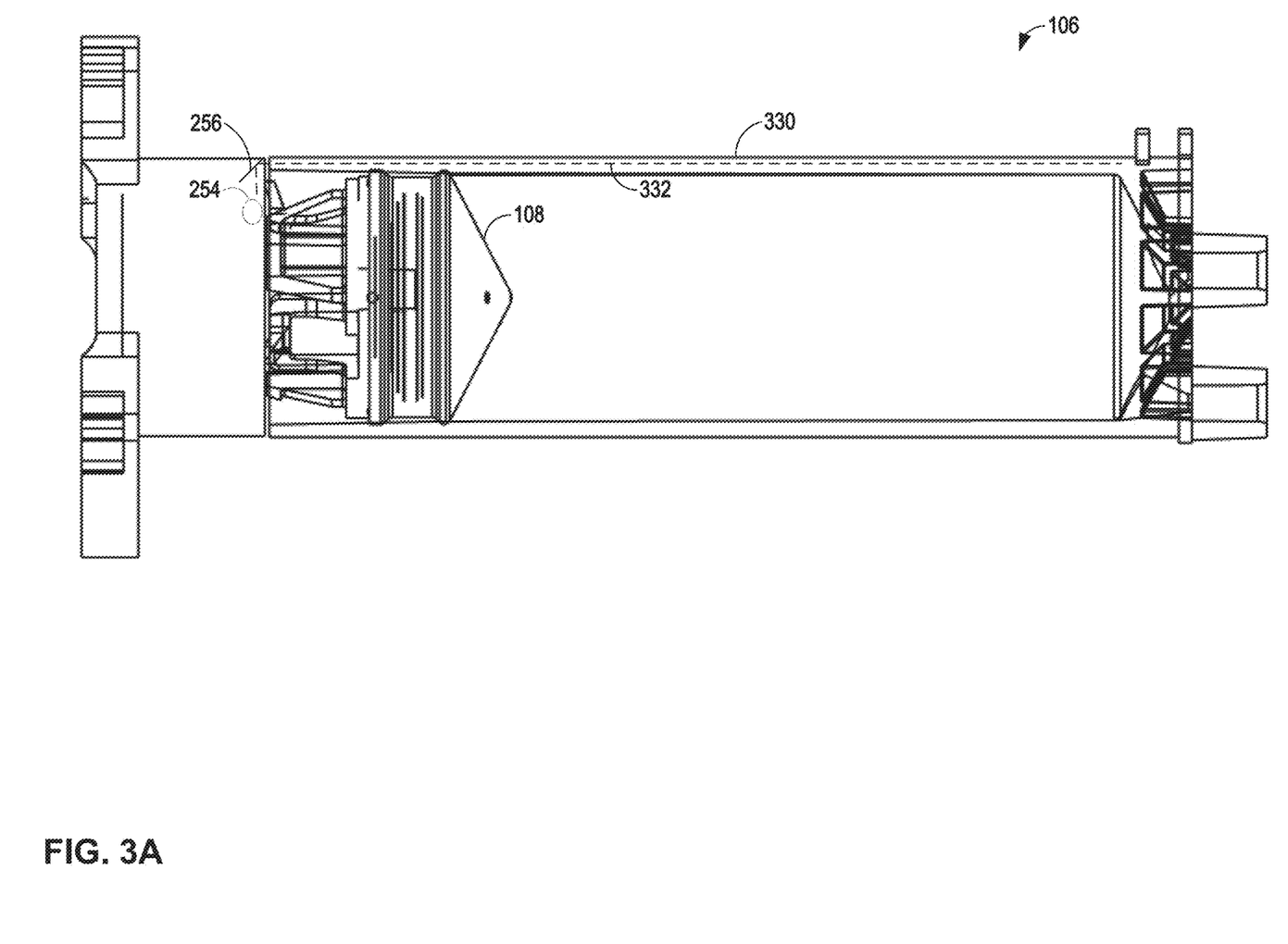
FIGS. 3A-3E are side views of various examples of a fluid reservoir and a light configured to illuminate an interior of the fluid reservoir, in accordance with one or more aspects of the techniques described in this disclosure.

FIG. 3A shows a side view of fluid reservoir 106. In the example of FIG. 3A, lights 254 are located behind plunger 108 within the housing. Lights 254 may be configured to direct light 332 radially outwardly into reflector 256. Reflector 256 may be angled such that the light 332 received from lights 254 is reflected through one or more clear portions of the housing, fluid reservoir 106, and plunger 108 and into peripheral wall 330 of fluid reservoir 106. Reflector 256 may further be angled such that light 332, when reflected off reflector 256, illuminates the interior of fluid reservoir 106 by travelling through peripheral wall 330. This particular implementation may have the additional benefit of easing the identification of any bubbles that may exist within the fluid housed within fluid reservoir 106. The bubbles may float to the top of fluid reservoir 106 such that the bubbles would rest along the top-most portion of peripheral wall 330, meaning that light 332 would run through the bubbles as it travels along peripheral wall 330.

Figure 3B:
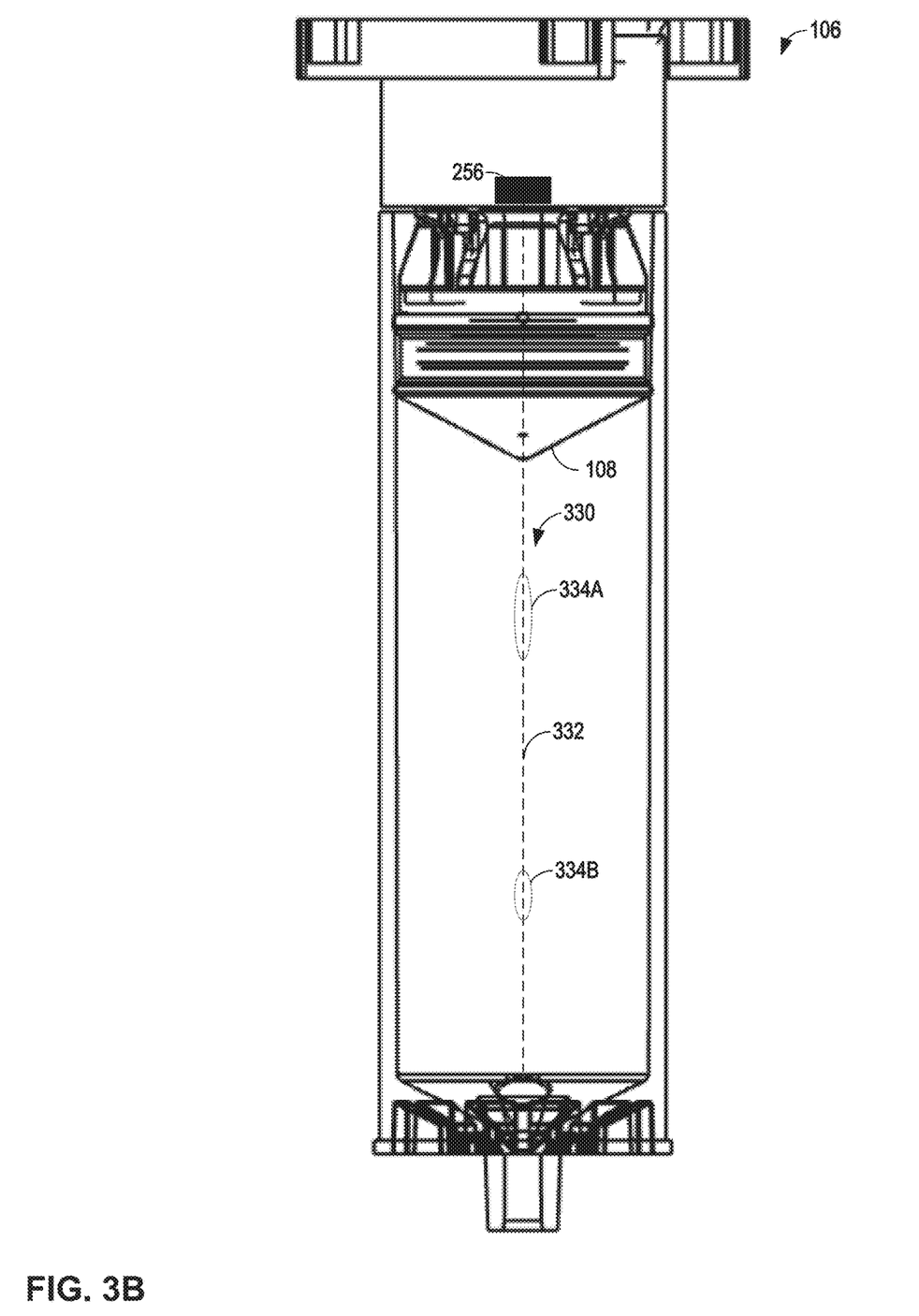

FIG. 3B is a top view of fluid reservoir 106 when bubbles 334A-334B are present within the fluid held within fluid reservoir 106. Similar to the example of FIG. 3A, the light source is directing light 332 upwards towards reflector 256. Reflector 256 reflects light 332 along top peripheral wall 330 of fluid reservoir 106. As light 332 travels along peripheral wall 330, light 332 passes through bubbles 334A and 334B. As light 332 passes through bubbles 334A and 334B, bubbles 334A and 334B become more evident to an operator of the fluid injection system such that the operator can cease the injection of the fluid into the patient due to the presence of bubbles 334A and 334B.

Figure 3C:
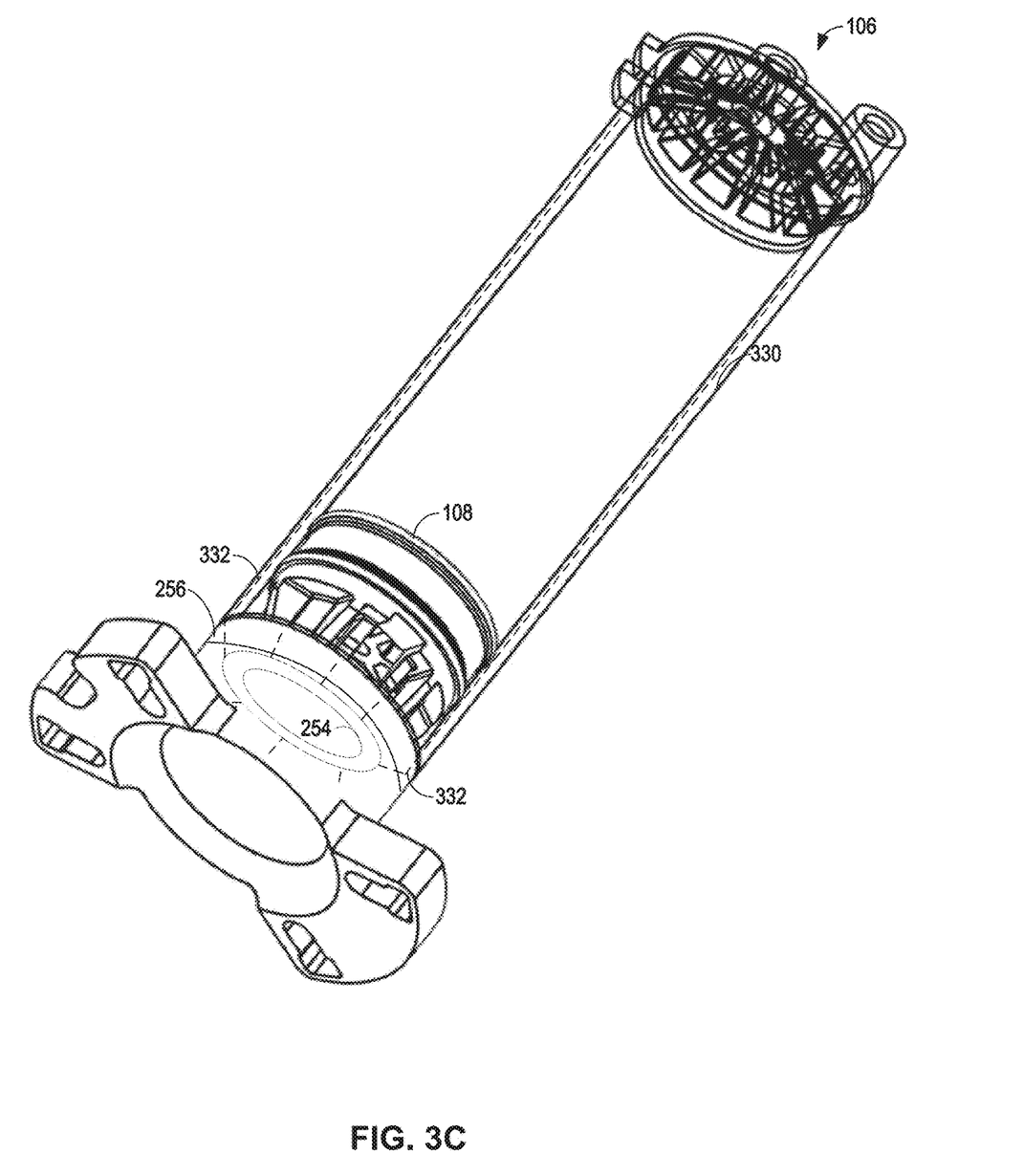

FIG. 3C shows a perspective view of fluid reservoir 106. In the example of FIG. 3C, lights 254 form a ring behind plunger 108 within the housing. Lights 254 may be configured to direct light 332 outwardly into reflector 256, which forms a circle around the interior of fluid reservoir 106 behind plunger 108 and peripheral wall 330. Reflector 256 may be angled such that the light 332 received from lights 254 is reflected through one or more clear portions of the housing, fluid reservoir 106, and plunger 108 and into the entirety of the circumference of peripheral wall 330. Reflector 256 may further be angled such that light 332, when reflected off reflector 256, illuminates the interior of fluid reservoir 106 by travelling through the entire circumference of peripheral wall 330. This particular implementation may have the additional benefit of easing the identification of any bubbles that may exist within the fluid housed within fluid reservoir 106. The bubbles may float to the top of fluid reservoir 106 such that the bubbles would rest along the top-most portion of peripheral wall 330, meaning that light 332 would run through the bubbles as it travels along peripheral wall 330.

Figure 3D:
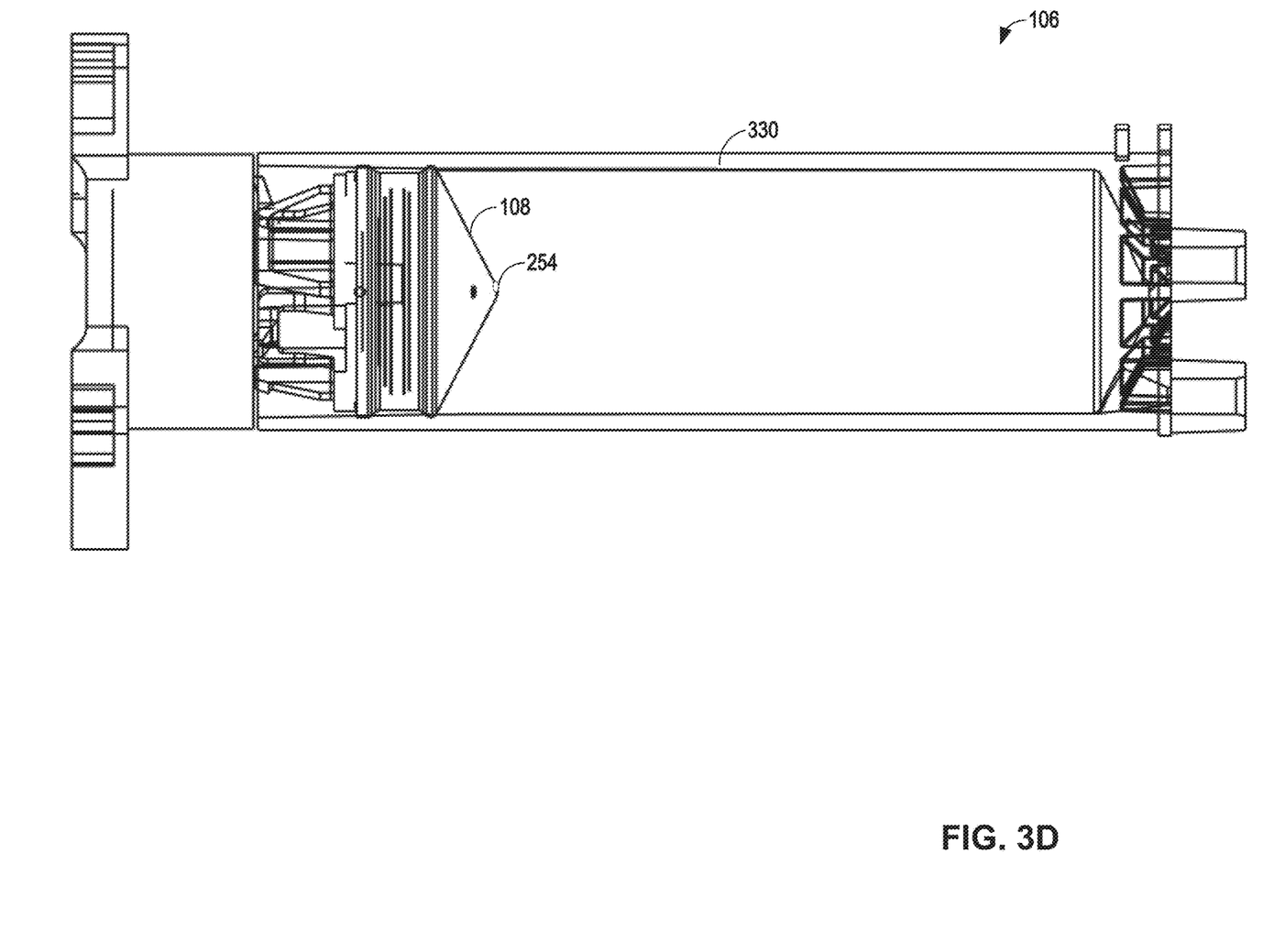

FIG. 3D shows a side view of fluid reservoir 106. In the example of FIG. 3D, light 254 is on the tip of plunger 108. Being located in the center of fluid reservoir 106 and in contact with any fluid stored in fluid reservoir 106, when lights 254 are activated, light may be emitted from lights 254 and diffused throughout the fluid. In this way, it would be clear to an operator of the fluid injection system as to any characteristics of lights 254, such as characteristics that may signify an operating status of the fluid injection system. Further, by placing lights 254 on plunger 108, lights 254 would remain in contact with the fluid held within fluid reservoir 106 throughout the process of plunger 108 exerting force on the fluid to push the fluid out of fluid reservoir 106.

Figure 3E:
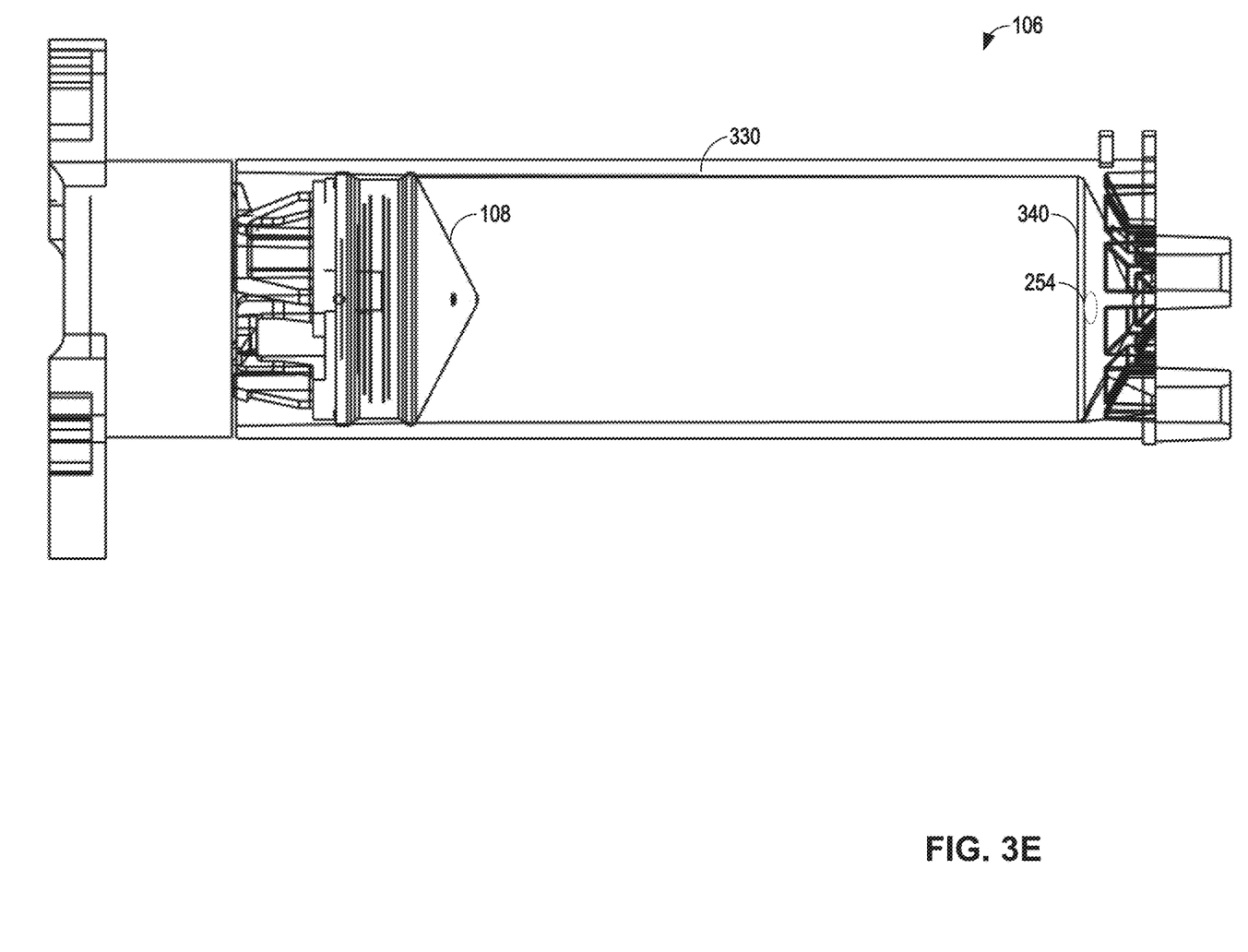

FIG. 3E shows a side view of fluid reservoir 106. In the example of FIG. 3E, light 254 is on receiver 340 of where plunger 108 would ultimately rest once plunger has moved completely through fluid reservoir 106 and expelled all of the fluid out of fluid reservoir 106. Being located in the center of fluid reservoir 106 and in contact with any fluid stored in fluid reservoir 106, when lights 254 are activated, light may be emitted from lights 254 and diffused throughout the fluid. In this way, it would be clear to an operator of the fluid injection system as to any characteristics of lights 254, such as characteristics that may signify an operating status of the fluid injection system. Further, by placing lights 254 on receiver 340 of plunger 108, lights 254 would remain in contact with the fluid held within fluid reservoir 106 throughout the process of plunger 108 exerting force on the fluid to push the fluid out of fluid reservoir 106.

Figure 4A:
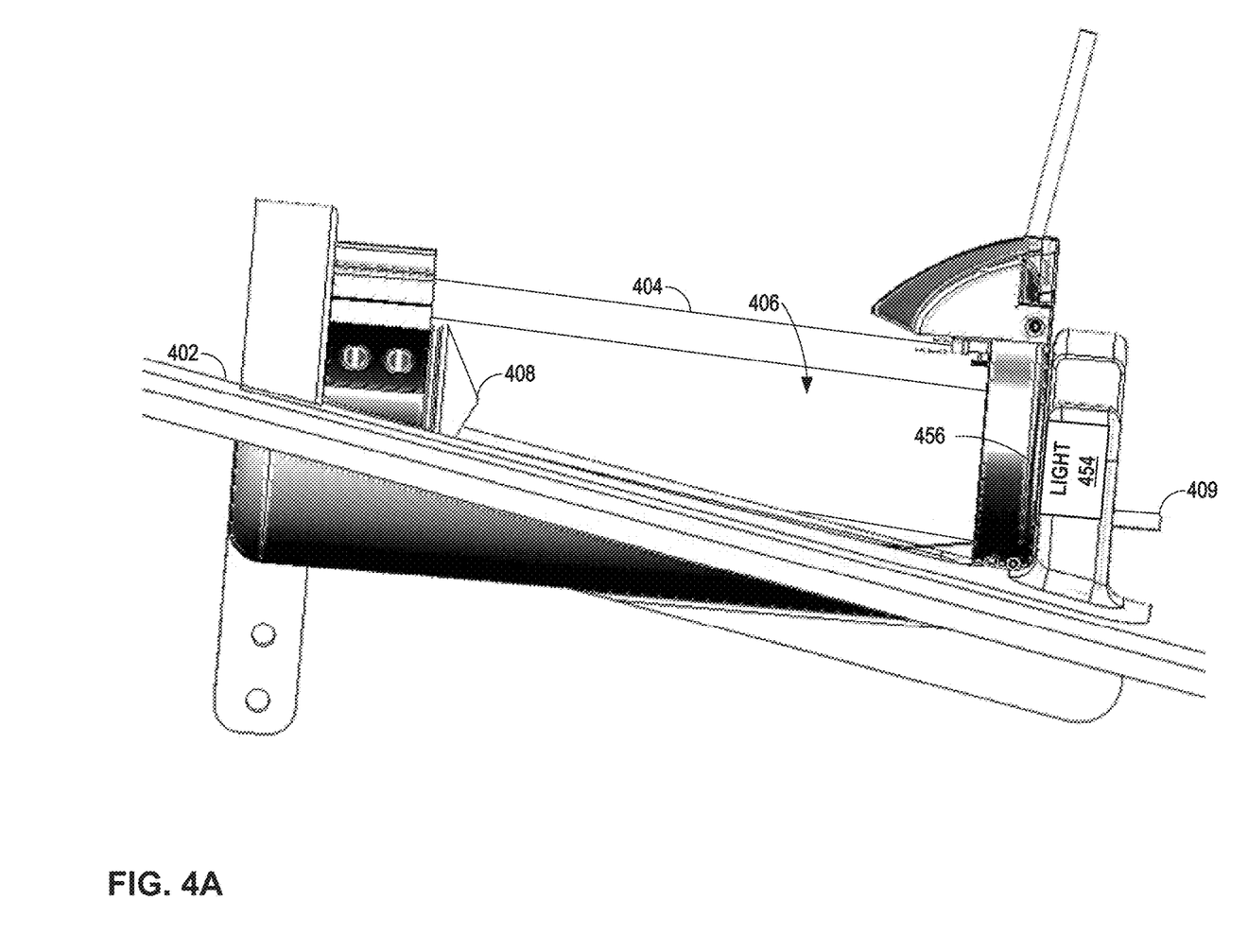
FIGS. 4A-4B are side views of additional examples of a fluid reservoir and a light configured to illuminate an interior of the fluid reservoir, in accordance with one or more aspects of the techniques described in this disclosure.
Figure 4B:
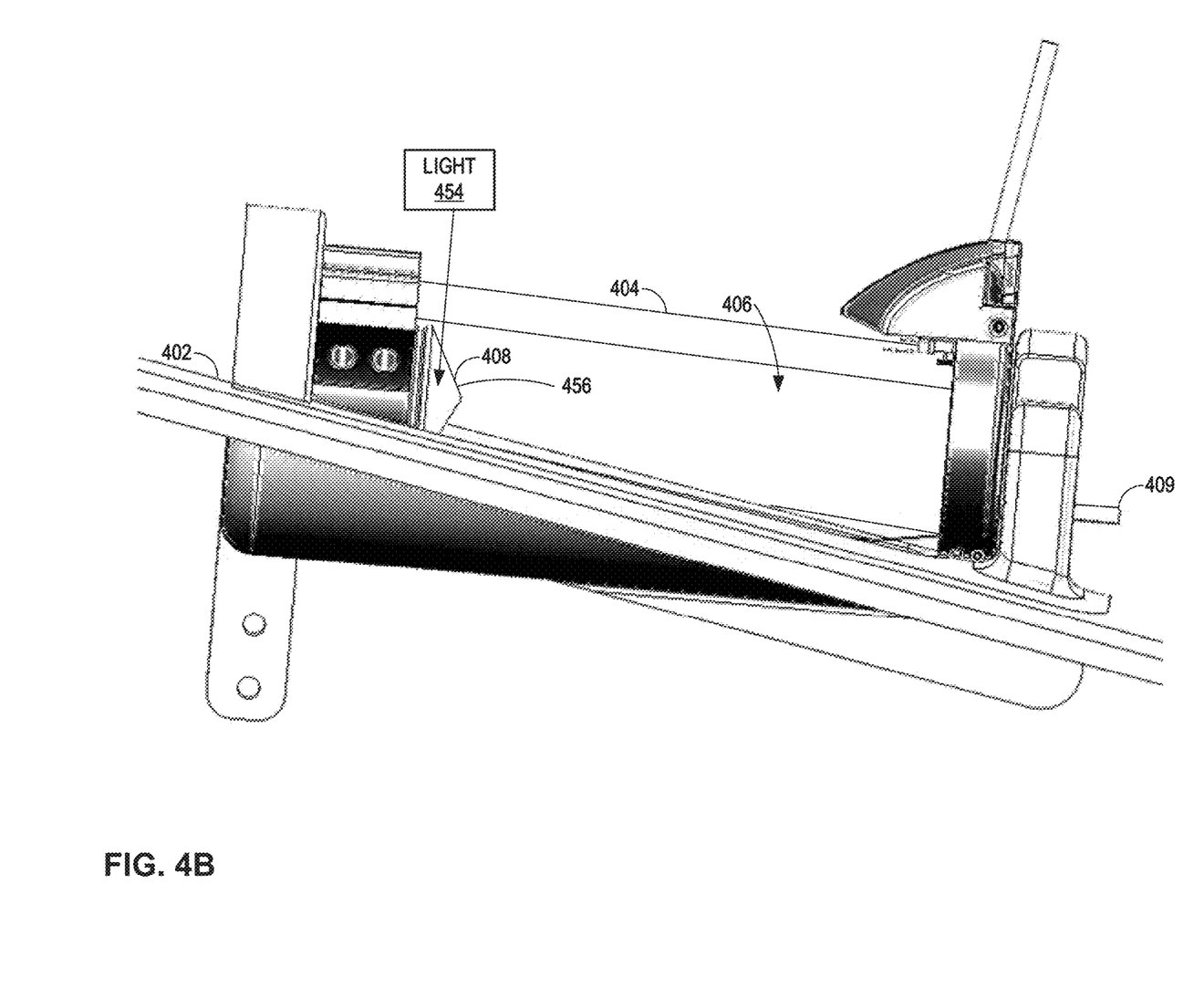
Figure 5A:
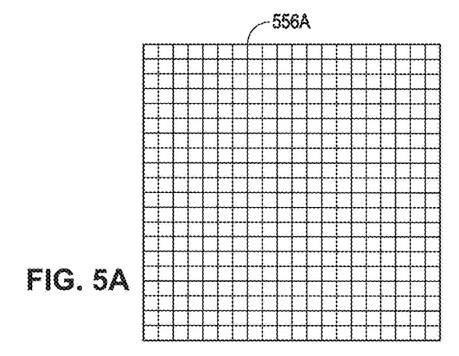
FIG. 5A-5F includes multiple diagrams of potential patterns for a light diffuser configured to diffuse the light, in accordance with one or more aspects of the techniques described in this disclosure.
Figure 5B:
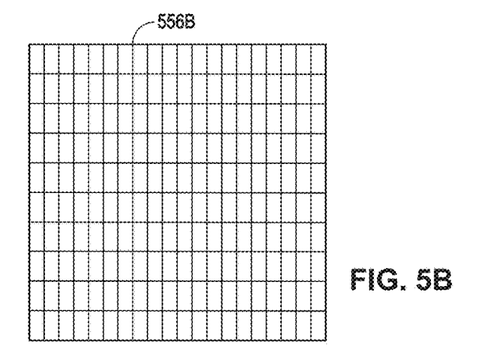
Figure 5C:
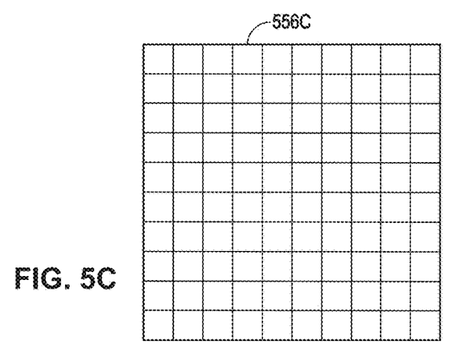
Figure 5D:
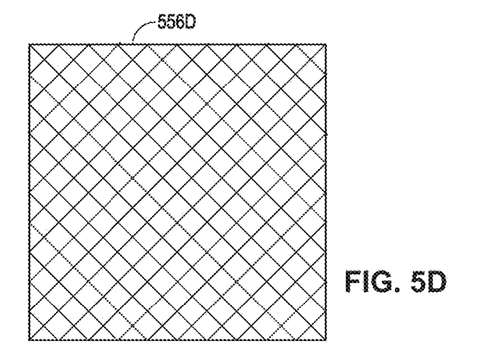
Figure 5E:
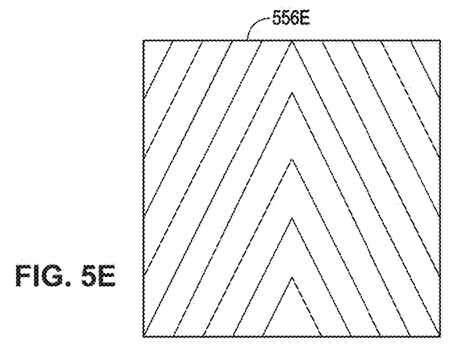
Figure 5F:
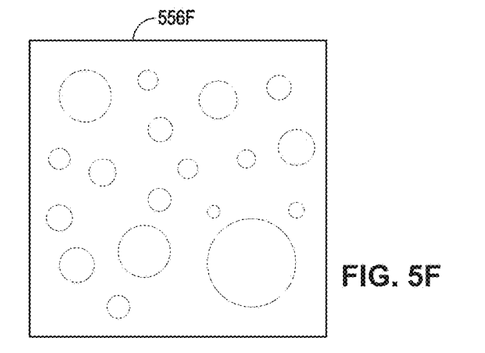

FIGS. 4A-4B are side views of additional examples of a fluid reservoir and a light configured to illuminate an interior of the fluid reservoir, in accordance with one or more aspects of the techniques described in this disclosure. In each of FIGS. 4A and 4B, housing 402 holds pressure sleeve 404 in place. Inside pressure sleeve 404, fluid reservoir 406 (also known as a syringe) is installed. Upon the activation of plunger 408, fluid held within fluid reservoir 406 exits the reservoir from catheter 409.

In the example of FIG. 4A, light 454 is included in housing 402 at a location near the end of fluid reservoir 406 opposite plunger 408 (e.g., the end which plunger 408 moves toward upon activation to expel the fluid from fluid reservoir 406). Light 454 is angled such that it emits light substantially parallel to a long axis of fluid reservoir 406. Being substantially parallel to the long axis may mean that the light, when it is emitted from light 454, is on a projected path that is within a small deviation of being parallel to the long axis, such as within fifteen degrees of a line that would be parallel to the long axis of fluid reservoir 406.

Diffusion element 456 may be situated between light 454 and fluid reservoir 406 such that the light emitted from light 454 is diffused, spreading throughout the fluid of fluid reservoir 406 to illuminate the interior of fluid reservoir 406. For instance, diffusion element 456 may be installed in housing 402, pressure sleeve 404, fluid reservoir 406, or any space in between any of those elements such that the light arrives at diffusion element 456 prior to entering fluid reservoir 406. Diffusion element 456 may be made of a clear material, or at least include a pattern of a substantially translucent material that diffuses the light as it passes through the diffusion element. For instance, diffusion element 456 may be at least partially made of a material such as a clear plastic, silicone, glass, frosted glass, or any other material that substantially allows light to pass through it. The pattern in diffusion element 456, such as a waffle pattern or bubble pattern, may further enable the diffusion of the light as it passes through diffusion element 456.

The example of FIG. 4B includes the same elements as the example of FIG. 4A, except that light 454 is installed in plunger 408. In this way, light 454 emits light out of plunger 408 and into fluid reservoir 406 as plunger 408 moves through fluid reservoir 406. In this example, diffusion element 456 is also located in plunger 408, either between light 454 and a surface of plunger 408 or directly on the surface of plunger 408. In this way, diffusion element 456 can spread the light emitted by light 454 throughout fluid reservoir 406.

FIGS. 5A-5F include multiple diagrams of potential patterns for a light diffuser configured to diffuse the light, in accordance with one or more aspects of the techniques described in this disclosure. For instance, diffusion element 556A includes a squared waffle pattern embedded in the material of diffusion element 556A. Diffusion element 556B includes a rectangular pattern embedded in the material of diffusion element 556B. Diffusion element 556C includes a squared waffle pattern embedded in the material of diffusion element 556C, but with the squares larger than that of diffusion element 556A. Diffusion element 556D includes a diamond pattern embedded in the material of diffusion element 556D. Diffusion element 556E includes a chevron pattern embedded in the material of diffusion element 556E. Diffusion element 556F includes a bubble pattern embedded in the material of diffusion element 556F.

In some instances, the patterns in diffusion elements 556A-556F may be textures, with the lines representing portions of the respective diffusion element that are either raised or lowered from the white space in the respective diffusion element. In other instances, the lines in the pattern may be a solid material, and the white space may represent translucent material. In still other instances, the lines in the pattern may be a translucent material, and the white space may be a solid material. Diffusion elements 556A-556F also represent only a few examples of potential patterns in a diffusion element. The diffusion element made in accordance with the techniques of this disclosure may include any pattern or arrangement of translucent material that would adequately diffuse light entering a fluid reservoir such that the light illuminates the interior of the fluid reservoir after diffusion.

Figure 6:
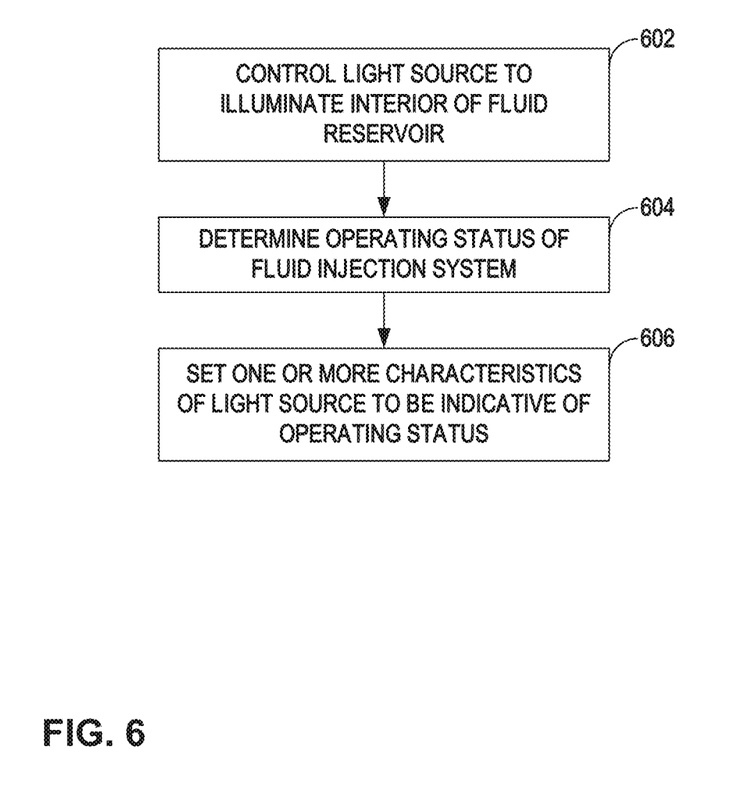
FIG. 6 is a flowchart illustrating an example process for a light source to illuminate an interior of a fluid reservoir in a fluid injection system based on an operating status of the fluid injection system, in accordance with one or more aspects of the techniques described in this disclosure.

FIG. 6 is a flowchart illustrating an example mode of operation. Particularly, FIG. 6 is a flowchart illustrating an example process for a light source to illuminate an interior of a fluid reservoir in a fluid injection system based on an operating status of the fluid injection system, in accordance with one or more aspects of the techniques described in this disclosure. The techniques of FIG. 6 may be performed by one or more processors of a computing device, such as powered fluid injector 100 of FIG. 1 and/or powered fluid injector 100 illustrated in FIG. 2. For purposes of illustration only, the techniques of FIG. 6 are described within the context of powered fluid injector 100 of FIG. 2, although computing devices having configurations different than that of powered fluid injector 100 may perform the techniques of FIG. 6.

In accordance with the techniques described herein, lighting module 220 controls a light source in a lighting assembly of the fluid injection system to illuminate an interior of a fluid reservoir secured by a sleeve coupled to an injector housing of the fluid injection system (600). Injection module 222 determines an operating status of the fluid injection system (602). Lighting module 220 sets one or more characteristics of the light source to be indicative of the operating status of the fluid injection system (604).

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

Various examples of the disclosure have been described. Any combination of the described systems, operations, or functions is contemplated. These and other examples are within the scope of the following claims.

What is claimed is:

1. A fluid injection system comprising:
   an injector housing;
   a sleeve coupled to the injector housing, wherein the sleeve is configured to receive and secure a fluid reservoir, wherein the fluid reservoir further comprises a wiper that is proximally and distally movable within the interior of the fluid reservoir;
   a ram extending from the injector housing into the sleeve, the ram being configured to engage the wiper when the fluid reservoir is secured in the sleeve and to drive the wiper proximally and distally in accordance with instructions received from an injection controller coupled to the injector housing;
a light source disposed on the injector housing proximate a distal end of the fluid reservoir relative to the wiper when the fluid reservoir is secured in the sleeve and the wiper is not extended, the light source configured to emit light into an interior of the fluid reservoir in a direction substantially parallel to a long axis of the fluid reservoir; and
a diffusion element located between the light source and the fluid reservoir, wherein the light emitted by the light source passes through the diffusion element, and wherein the diffusion element is configured to diffuse the light emitted by the light source in order to illuminate the fluid reservoir, wherein the diffusion element comprises a substantially translucent material having a pattern of raised or lowered portions.

2. The fluid injection system of claim 1, further comprising one or more processors configured to control one or more characteristics of the light source when illuminating the interior of the fluid reservoir.

3. The fluid injection system of claim 2, wherein the one or more characteristics of the light source include one or more of a brightness, a color, a flashing pattern, or a number of individual lights within the light source to be illuminated.

4. The fluid injection system of claim 2, wherein the one or more processors are further configured to:
   determine an operating status of the fluid injection system; and
   set the one or more characteristics of the light source to be indicative of the operating status of the fluid injection system.

5. The fluid injection system of claim 4, wherein the operating status of the fluid injection system comprises one or more of an injection rate, a volume of fluid contained in the fluid reservoir, an air bubble detection mode, an injection mode, a refill rate, or an error status.

6. The fluid injection system of claim 2, wherein the one or more processors control the one or more characteristics of the light source based on instructions received from the injection controller coupled to the injector housing.

7. The fluid injection system of claim 1, wherein the fluid reservoir comprises a peripheral wall that defines the interior of the fluid reservoir,
   wherein the peripheral wall extends between a proximal edge of the fluid reservoir and a distal edge of the fluid reservoir.

8. The fluid injection system of claim 1, wherein the light source comprises one or more light-emitting diodes.

* * * * *